United States Patent
Gist et al.

(10) Patent No.: US 10,493,189 B2
(45) Date of Patent: Dec. 3, 2019

(54) MFLP-VALVE FOR A PRESSURE SOURCE

(71) Applicant: MEDELA HOLDING AG, Baar (CH)

(72) Inventors: Jahi Gist, Barrington, IL (US); David Cho, Arlington Heights, IL (US); Mario Rigert, Buchrain (CH)

(73) Assignee: MEDELA HOLDING AG, Baar (CH)

( * ) Notice: Subject to any disclaimer, the term of this patent is extended or adjusted under 35 U.S.C. 154(b) by 680 days.

(21) Appl. No.: 15/235,370

(22) Filed: Aug. 12, 2016

(65) Prior Publication Data
US 2017/0043073 A1    Feb. 16, 2017

Related U.S. Application Data

(60) Provisional application No. 62/205,419, filed on Aug. 14, 2015.

(51) Int. Cl.
*A61M 1/06* (2006.01)
*A61M 39/22* (2006.01)
*A61M 39/24* (2006.01)

(52) U.S. Cl.
CPC .............. *A61M 1/062* (2014.02); *A61M 1/06* (2013.01); *A61M 39/227* (2013.01); *A61M 2039/2486* (2013.01); *A61M 2205/332* (2013.01); *A61M 2205/3331* (2013.01); *A61M 2205/3337* (2013.01)

(58) Field of Classification Search
CPC .................. A61M 1/06; A61M 1/0072; A61M 2205/3331; A61M 2205/3337; A61M 1/062; A61M 2039/2486
See application file for complete search history.

(56) References Cited

U.S. PATENT DOCUMENTS 6,663,587 B2 *  12/2003  Silver ................... A61M 1/064
                                                                    119/14.47
2007/0292276 A1  12/2007  Stutz et al.
2009/0275922 A1  11/2009  Coulthard et al.
(Continued)

FOREIGN PATENT DOCUMENTS

WO    WO-2015/075158 A1    5/2015

OTHER PUBLICATIONS

International Preliminary Report on Patentability and Written Opinion of the International Searching Authority for Application No. PCT/US2016/046683, dated Feb. 20, 2018.

*Primary Examiner* — Nathan R Price
*Assistant Examiner* — Anh Bui
(74) *Attorney, Agent, or Firm* — Marshall, Gerstein & Borun LLP (57) ABSTRACT

A mechanical fluid pressure modification valve, or "MFLP-valve", is set forth. The MFLP-valve can be actuated upon movement of a movable pressure system member of a medical pressure system reaching a selected position. Additionally, the MFLP-valve can be actuated based on a pressure condition of the system. When the MFLP-valve unseals, a pressure differential between a pressure chamber and a volume outside of the chamber can be relieved. Disengagement of the movable pressure system member from the MFLP-valve can enable the MFLP-valve to re-seal. The MFLP-valve may include a flag that indicates the position of the movable pressure system member. The MFLP-valve may be provided in a diaphragm-type pressure source.

11 Claims, 7 Drawing Sheets

(56) References Cited

U.S. PATENT DOCUMENTS

| | | |
|---|---|---|
| 2013/0294942 A1 | 11/2013 | Stutz et al. |
| 2014/0227112 A1* | 8/2014 | Felber .................. A61M 1/0066 417/53 |
| 2014/0276629 A1* | 9/2014 | Bauer ..................... A61M 1/06 604/514 |
| 2015/0119691 A1 | 4/2015 | O'Neill et al. |

* cited by examiner

MFLP-VALVE FOR A PRESSURE SOURCE

CROSS-REFERENCE TO RELATED APPLICATION

This application claims priority to U.S. Provisional Patent Application No. 62/205,419 filed Aug. 14, 2015 entitled "MFLP-Valve for a Pressure Source," the entire disclosure of which is hereby expressly incorporated by reference herein.

FIELD OF THE DISCLOSURE

The present disclosure relates generally to pressure systems, such as breastmilk expression systems, including breastpumps, and, more particularly, to a mechanical fluid pressure modification valve (hereinafter MFLP-valve) that provides relief and/or intake for fluid in a pressure system, and that may be used in combination with a flag selectively detected by a sensor.

BACKGROUND

Pressure systems, such as breastmilk expression systems, have been disclosed that include mechanisms to selectively modify pressure within the system. For instance, U.S. Pat. No. 5,007,899 discloses a breastpump with a piston pump having an aperture in a piston cylinder. The breastpump exposes the vacuum generating chamber to atmosphere when the head of the piston passes beyond the aperture. This returns the chamber to ambient pressure and limits peak negative pressure.

U.S. Pat. No. 8,070,715 discloses a breastpump system having a solenoid valve provided in an ambient airline. The solenoid valve is operated by a controller to open when a vacuum in a breastshield of the breastpump system reaches a desired pressure, permitting the vacuum within the breastshield to decrease (in other words, permitting the pressure in the breastpump system to increase) toward ambient pressure. However, instead of allowing the vacuum to decrease all the way to ambient pressure, the breastpump is further provided with a regulator that closes during breastpump operation once the system reaches a preset minimum vacuum level.

The known pressure control mechanisms may require more than desired design complexity. For example, the piston-cylinder/aperture design may limit the overall performance of the system. The solenoid valve needs to be powered directly. The solenoid valve also adds cost to the system, and may generate undesirable noise in the system. For these and other reasons, previously-designed pressure control systems may introduce limitations for optimizing the design.

SUMMARY OF THE DISCLOSURE

In accordance with the principles of the present disclosure, a mechanical fluid pressure modification valve, or MFLP-valve, is set forth. One or more MFLP-valves can be customized, or tuned, to fine tune fluid flow in a pressure system. The MFLP-valve may be integrally formed within a surface of the pressure system. The MFLP-valve can be formed of an expandable material, and can be vented or selectively vented. For example, where the MFLP-valve is an expandable member, the expandable portions of the MFLP-valve can include one or more vents that only open upon expansion of the MFLP-valve, thereby selectively venting the system. The MFLP-valve can be non-electric.

The MFLP-valve may comprise an operable cover configured to cause a pressure condition in the system. The operable cover may be disposed above an aperture of the pressure system and may be composed of a lightweight material. The operable cover of the MFLP-valve may be connectable to the pressure system to modify system pressure therethrough, for example, to vent the system to ambient pressure. The operable cover may achieve this by having one or more vents formed within the operable cover, the vents configured to enable fluid flow into or out of the pressure system. The vents may be expansion vents, which are vents that open when the operable cover moves, or relief vents, or both. The operable cover may be configured to open based on a mechanical change in the pressure system.

The MFLP-valve, and specifically the operable cover, can incorporate a post that can be selectively engaged by a movable pressure system member. The MFLP-valve can provide both relief and intake in a pressure system. The pressure system may act as a closed pressure system, except when the MFLP-valve is active. Additionally, the MFLP-valve can provide information regarding a state of the pressure system. To this end, one or more suitable detection devices, such as a sensor (such as a photoelectric sensor or a Hall effect position sensor) or switch, can be incorporated into the pressure system to determine an operating state of the MFLP-valve, based on an open or closed state of the MFLP-valve. The state determination can be made directly based on sensing the state from the MFLP-valve position or from a position indicator extending from the MFLP-valve. Alternatively, the state determination can be made indirectly based on a cooperating position member whose movement is coordinated with changes in state of the MFLP-valve and detected by one or more detection devices.

In an exemplary embodiment constructed in accordance with the principles of the present disclosure, a pressure system, such as a breastmilk expression system, can include one or more MFLP-valves attached to the pressure system, such as along a pressure generating chamber of the system. The MFLP-valve can provide a vent from an interior of the chamber to fluid outside of the chamber. The MFLP-valve can operate based on movement of a movable pressure system member, such as a pressure source or other system component, or member, for which an operational state can be monitored based on the movement of the component. The MFLP-valve may be used to initialize the pressure source. The desired base pressure may be atmospheric pressure. Alternately, the desired base pressure may be a pressure other than atmospheric pressure. The MFLP-valve can also be configured to serve as a pressure relief mechanism that does not require contact with the movable pressure system member.

One example of why the desired base pressure might differ from atmospheric pressure is to minimize repetitive friction on a nipple as it is received in a nipple tunnel of a breastshield during repeated cycles of a vacuum source. For example, it has been observed that when an infant is properly latched onto a mother's breast during feeding, the nipple is held in a substantially constant depth in the infant's mouth relative to the junction of the hard and soft palette. In an effort to mimic this natural action, it may be desirable to hold at least a minimum vacuum that is less than atmospheric pressure, during successive cycles of the vacuum.

A MFLP-valve constructed in accordance with the principles herein can operate by movement of a movable pressure system member of a pressure source. In an exemplary embodiment, the MFLP-valve can provide verification of a position of the movable pressure system member when actuated. To this end, a MFLP-valve constructed in accordance with the principles herein can include structure or related components in the pressure system, any of which can be configured to provide condition state information to one or more detection devices or systems in the pressure system.

For example, in one embodiment, the MFLP-valve can include an extension, such as a flag, configured to selectively engage a sensor dependent upon a position of the flag relative to the position of the movable pressure system member. The flag can be operably connected to and/or extend from an operable cover of the MFLP-valve. In one embodiment, engagement between the flag and the sensor indicates that movable pressure system member is in a desired position indicative of an operating condition. For example, when the movable pressure system member is in a position that causes the MFLP-valve to be in an open position, the flag on the MFLP-valve may be moved into a location in which it can be sensed by a sensor, such as by having a beam of light hit the flag. In another embodiment, dis-engagement between the flag and the sensor indicates that the movable pressure system is in a desired position indicative of an operating condition. For example, the flag may have a hole or port in it. The flag may normally be engaged with the sensor (for example, by being hit by a beam of light), but movement of the MFLP-valve in response to the location of the movable pressure system member may cause the sensor to disengage with the flag (for example, by having the beam of light pass through the hole.) In this embodiment, the dis-engagement between the flag and the sensor indicates the position of the movable pressure system member. In yet another embodiment, the flag can be configured to engage a switch or other component when a desired position indicative of an operating condition is reached by the flag in the system.

In another embodiment, a sensor may be capable of sensing more than whether the flag is engaged or disengaged with the sensor and can provide more detailed information about the location of the movable pressure system member. For example, different and specific stripes on a flag, where each specific stripe corresponds with a certain position of the movable pressure system member, may be sensed by a sensor and used to provide specific information about the location of the movable pressure system member. By using this or similar techniques, the speed at which the pressure system member is moving can also be determined if desired.

In still another embodiment, the flag can be configured to indicate a mechanical state change, such as whether the pressure system is open or closed, in the pressure system to a detection device or detection system. In other embodiments, or in combination with one or more embodiments herein, the flag can be configured to verify the output of other sensors incorporated into the system, including, but not limited to position, speed, pressure and/or state change sensors. In a further embodiment, the MFLP-valve can be formed of elastic and/or expandable material configured to be movable between a closed state and an open state, where the flag either opens or expands and the detection device or detection system is configured to detect the open state of the MFLP-valve. Examples of suitable elastic and/or expandable materials can include elastic, rubber, spring-like material, or any other expandable material. Alternatively, the detection device or detection system can be configured to detect the closed state of the MFLP-valve.

In yet another embodiment, an associated component of the system can be configured to relay the position of the MFLP-valve to the detection device or detection system, so that a direct sensing of the MFLP-valve or a flag extending therefrom, is not required. The flag or associated component indicating a state condition to a detection device or detection system can indicate any position information desired from the system, or a pressure change or condition.

A MFLP-valve constructed in accordance with the principles of the present disclosure can be varied, adjusted, customized, or tuned, as desired, by changing the geometry and/or material properties of the MFLP-valve in order to adjust, for example, the force required to open the MFLP-valve and/or the response of the position indicator. In this manner the accuracy, precision, sensitivity, or other parameter(s) of the MFLP-valve can be selected to suit a particular pressure system. For example, sealing characteristics of the MFLP-valve can be tuned by adjusting the material and/or geometry of the MFLP-valve. In addition, fluid flow rate for the system can be varied by varying the number and size of relief apertures, or vents, provided in the MFLP-valve. Still further, the relief apertures, or vents, can be selectively openable, such as by expanding the MFLP-valve, if desired. In accordance with a method of manufacture, sealing capabilities of the MFLP-valve can be selected based on performance capabilities or other configurations of the system, including pressure parameters of the system as well as a selection of the number of MFLP-valves to be used in a system. As yet another example, the MFLP-valve may be tuned and configured to open with a delayed action when the movable pressure system member engages the MFLP-valve, and the MFLP-valve may further being tuned and configured to remain open with a delayed action before returning to a first, sealed position when the movable pressure system member is disengaged from the MFLP-valve. The MFLP-valve can be constructed so as to change shape in response to changing pressure or the movable pressure system member, and the shape change may create an opening that relieves system pressure or indicate a change in the position of the movable pressure system member. The tuned properties of the MFLP-valve may be collectively referred to as the "tuning condition".

In accordance with the principles herein, the system can include a MFLP-valve that includes a preset tuning condition, determined prior to manufacturing of the system. In another embodiment, the system can be tuned by altering properties of the MFLP-valve during the manufacturing process, including on unit by unit basis, if desired. In still another embodiment of the system, the tuning condition of the MFLP-valve can be linked to the pressure system's mode of operation at any given time, such that the user may directly or indirectly change the MFLP-valve tuning condition as the systems mode of operation is changed. Changes to the tuning condition of the MFLP-valve can be reversible, if desired.

According to embodiments within the scope of the present disclosure, a medical pressure system includes a mechanical fluid pressure modification valve, referred to herein as a "MFLP-valve," that selectively seals and unseals an aperture through which, when unsealed, a pressure differential between a pressure chamber within the pressure system and a volume outside of the pressure system is minimized until a desired pressure is obtained; a controller in operable communication with a pressure source of the pressure system; and a flag connected to the MFLP-valve, the flag configured to trigger at least one of (1) modify operation of the pressure source upon motion of the MFLP-valve between a sealed condition and an unsealed condition, and (2) verify a position of a movable pressure system member of the system.

The flag may be directly attached to the MFLP-valve. Alternately, the flag may be indirectly attached to the MFLP-valve. The MFLP-valve may include a gasket to seal the aperture. In sealingly engaging a wall of the pressure source about a perimeter of the aperture, the gasket sealingly engages an end wall of the pressure source.

A breastmilk expression system of the present disclosure includes a MFLP-valve configured to minimize a pressure differential between a pressure generating chamber and a volume outside the pressure generating chamber through an aperture; and a movable pressure system member disposed in the system, the movable pressure system member configured for movement between a first position and a second position, the MFLP-valve actuable to an open position upon the movable pressure system member reaching the second position and the MFLP-valve indicating a position to a sensor in the system. The MFLP-valve may be further configured to reach the open position to minimize a pressure differential irrespective of the position of the movable pressure system member. The aperture may be disposed within the pressure generating chamber, the MFLP-valve being actuable between a first, sealed position sealing the aperture and a second, open position unsealing the aperture.

The MFLP-valve may be configured to open when the movable pressure system member engages the MFLP-valve and the MFLP-valve may be further configured to return to the first, sealed position when the movable pressure system member is disengaged from the MFLP-valve. The MFLP-valve may be tuned and may open with a delayed action when the movable pressure system member engages the MFLP-valve, and the MFLP-valve may further be tuned and may remain open with a delayed action before returning to the first, sealed position when the movable pressure system member is disengaged from the MFLP-valve. The MFLP-valve may include a post extending through the aperture, the movable pressure system member being a reciprocating member, the post being engaged by the reciprocating member when the reciprocating member is in the second position.

The MFLP-valve may further include a membrane surrounding the post, the membrane having a surface area greater than an area of the aperture in the pressure generating chamber through which the post extends, such that upon disengagement of the post by the reciprocating member, the membrane closes over the aperture.

The MFLP-valve may further include a membrane surrounding the post, the membrane having a surface area greater than an area of the aperture in the pressure generating chamber through which the post extends, and a gasket depending from the membrane such that upon disengagement of the post by the reciprocating member, the gasket sealingly engages the pressure generating chamber about a perimeter of the aperture.

The MFLP-valve may include a living hinge, the living hinge hingedly securing the membrane to a portion of the MFLP-valve secured to the wall of the pressure generating chamber.

A breastmilk expression system of the present disclosure includes a MFLP-valve responsive to a mechanical force applied thereto, the MFLP-valve configured to open as a movable pressure system member arrives at a selected position and operably connects to the valve, thereby providing the mechanical force applied to the MFLP-valve.

A MFLP-valve of the present disclosure may include an operable cover connectable to a pressure chamber within a medical pressure system, configured to cause a pressure condition in the system upon movement of a movable pressure system member, and operably connected to a flag; and the flag may be configured to indicate a position of the movable pressure system member in the pressure system. The operable cover may be connectable to the pressure chamber within the pressure system to minimize a pressure differential between the pressure chamber and a volume outside of the pressure chamber.

The flag may be configured to selectively engage a sensor dependent on a position of the flag relative to the position of the movable pressure system member. The MFLP-valve may additionally include one or more vents configured to enable fluid flow into or out of the pressure chamber within the pressure system. Such vents may be formed in the operable cover, and the vents may be further defined by at least one of expandable vents and non-expandable vents.

The flag may be connected to, and extend from, the operable cover. The operable cover may further be configured to open based on a mechanical change in the pressure system.

A medical pressure system of the present disclosure includes a MFLP-valve including a operable cover connectable to a pressure chamber within the pressure system, and operably connected to a flag; and the flag configured to provide an indication of a position of a movable pressure system member in the system.

The medical pressure system may be a breastmilk expression system. The medical pressure system may further include a breastpump having a vacuum generating chamber. The vacuum generating chamber may include an aperture. The operable cover may be disposed above the aperture.

The operable cover may be dimensioned of a flexible material and configured to change pressure within the system upon operating.

The operable cover may further include a post, the vacuum generating chamber further including a movable pressure system member configured to selectively engage the post based on a position of the movable pressure system member within the vacuum generating chamber.

The vacuum generating chamber may further include a movable pressure member having a post, the post selectively engaging the operable cover based on a position of the movable pressure system member within the vacuum generating chamber.

A MFLP-valve of the present disclosure may include an operable cover; and a post connected to the operable cover and configured to extend into a fluid flow section of a medical pressure system, the post configured to engage an aperture of the pressure system during operation of the pressure system, the operable cover via the post configured to selectively open the aperture based on at least one of a position of a movable pressure system member in the system and a pressure condition in the pressure system. The pressure system used in connection with the MFLP-valve may be a breastpump, and the MFLP-valve may include a flag connected to the operable cover and configured to selectively engage a sensor when the movable pressure system member of the pressure system is in a desired position. The MFLP-valve may be configured to prevent fluid exchange through the MFLP-valve unless at least one of a selected position of the movable pressure system member in the pressure system has been reached and a pressure condition in the pressure system has been reached. At least one of geometry, material properties, or mating properties of the MFLP-valve can be adjustable to tune the accuracy, precision, sensitivity, or other parameter associated with the MFLP-valve upon a change in a mode of operation of the system. The MFLP-valve may be constructed so as to change shape in response to changing pressure or interaction with the movable pressure system member, and either the shape change creates an opening that relieves pressure in the pressure system or the shape change indicates a change in the position of the movable pressure system member. Moreover, a multi-pump system can be operated in accordance with the principles of the present disclosure.

The MFLP-valve may be integrally formed within a surface of the pressure system. The MFLP-valve may include a flag connected to an extending from a surface thereof.

A breastmilk extracting system of the present disclosure may include a pressure source configured to selectively activate one or more MFLP-valves based on the systems mode of operation. Such a breastmilk extraction system may be provided wherein each of the one or more MFLP-valves are configured for selective tuning to adjust fluid flow in the system based on a state of operation of the system. A breastmilk extracting system of the present disclosure may include an MFLP-valve operably connected to a pressure chamber of the system, the MFLP-valve configured to unseal to relieve a pressure differential between a pressure chamber of the system and a volume outside of the chamber by allowing fluid in the system to flow in and out of the MFLP-valve when the MFLP-valve unseals.

A system for extracting milk from a lactating human mother according to the present disclosure may include a breastpump, a pressure generating device including at least one of a piston and a diaphragm that generates pressure in the system, and a MFLP-valve that physically opens when the pressure generating device arrives at a return position at an end of a stroke of the pressure generating device. The pressure generating device physically opens the valve at the end of the stroke to connect the pressure in the system with external pressure, allowing the pressure in the system to equalize with external pressure or reducing a pressure differential between the system and external pressure.

An alternate embodiment of a pressure source of the present disclosure may include a diaphragm membrane, a rigid cap, a movable pressure system member associated with the diaphragm membrane that actuates the diaphragm membrane between a first position away from the rigid cap and a second position toward the rigid cap, and a MFLP-valve including an operable cover and a post connected to the operable cover, the post configured to engage an aperture of the pressure source during operation of the pressure source, the operable cover via the post configured to selectively open the aperture based on a position of at least one of the movable pressure system member and the diaphragm membrane. In such a pressure source, the aperture may be provided in the rigid cap, in which case the MFLP-valve is associated with the rigid cap, and the post extends through the aperture, so as to seal the aperture when the diaphragm membrane is not in contact with the post. Alternatively, the aperture may be provided in the diaphragm membrane, in which case the MFLP-valve is associated with the diaphragm membrane, and the post extends through the aperture, so as to seal the aperture when the post is not in contact with the rigid cap.

These and other advantages can be accomplished by a MFLP-valve constructed in accordance with the principles herein, as discussed in the following detailed description of the exemplary embodiments, with reference to the drawings.

DETAILED DESCRIPTION OF THE PREFERRED EMBODIMENTS

Figures 1, 2, 3, 4, 4A, 4B:
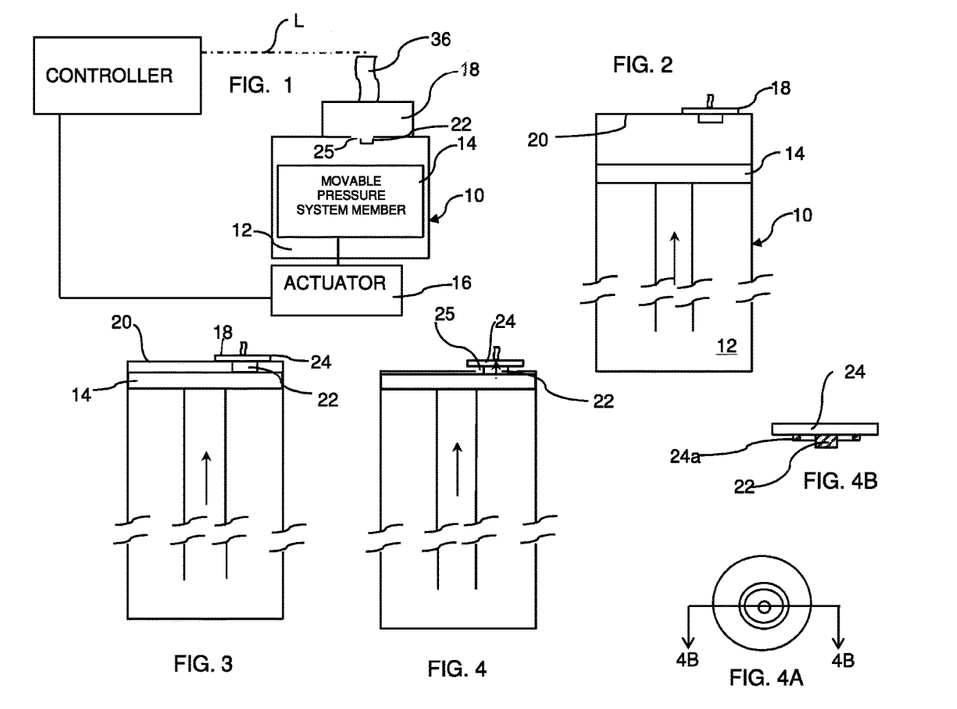
FIG. 1 is a schematic diagram of an exemplary pressure source provided with an exemplary embodiment of a MFLP-valve constructed in accordance with the principles of the present disclosure.
FIG. 2 illustrates an exemplary embodiment of an MFLP-valve in combination with a chamber of a pressure source having a movable pressure system member therein moving in a direction toward an end wall of the chamber.
FIG. 3 illustrates the chamber of the pressure source of FIG. 2 as the movable pressure system member continues to move in the direction toward the end wall of the chamber, and contacts an exemplary post of the MFLP-valve associated with the pressure source, causing the MFLP-valve to begin to move in the same direction as the movable pressure system member.
FIG. 4 illustrates the chamber of the vacuum source of FIGS. 2 and 3 as the movable pressure system member moves further in the direction toward the end wall of the chamber, causing the MFLP-valve to expose a region of an interior of the chamber between the movable pressure system member and the end wall of the chamber to an initializing pressure through an exemplary aperture in the end wall of the chamber.
FIG. 4A is a bottom view of an embodiment of a MFLP-valve constructed in accordance with the principles of the present disclosure.
FIG. 4B is an enlarged cross-section of the MFLP-valve taken along lines 4B-4B of FIG. 4A, the MFLP-valve having an annular rib defining a gasket or O-ring to facilitate sealing.

In accordance with the principles of the present disclosure, a pressure source, such as a pressure source 10 of a breastmilk expression device, for example, includes a pressure generating chamber 12 having a movable pressure system member 14 therein. The movable pressure system member may be actuated by an actuator 16, as illustrated in FIG. 1. A MFLP-valve 18 is associated with an end wall of the pressure generating chamber 12. As used herein, the term "MFLP-valve" refers to a pressure modification valve that can be configured to be coupled with a sensor flag, either directly or indirectly. The MFLP-valve 18 can be secured in a sealed relationship with an aperture 25 in a wall of the pressure generating chamber 12, or can otherwise be positioned as desired on or near the pressure generating chamber 12 or connected to a connector or tubing extending from the pressure generating chamber 12. In an embodiment, the MFLP-valve 18 can be displaced from a sealed condition to an unsealed condition relative to the aperture 25 by actuation of the movable pressure system member 14, or reciprocating member, from a first position to a second position, the MFLP-valve 18 actuable to an unsealed, open position upon the movable pressure system member 14 reaching the second position. By way of example only, the actuation of the MFLP-valve 18 from the sealed condition to the unsealed condition may be initiated by the movable pressure system member 14 coming into contact with, or engaging, a post 22 of the MFLP-valve 18 that extends through the aperture 25. As the movable pressure system member 14 approaches the aperture 25 associated with the pressure generating chamber 12, the movable pressure system member 14 engages the post 22. Continued actuation of the movable pressure system member 14 toward the aperture will urge the MFLP-valve 18 from a sealed condition to an unsealed condition relative to the aperture 25.

A "pressure differential" exists when the system pressure inside the chamber 12 differs from the pressure outside of the chamber 12. For example, vacuum generating systems, such as medical pumps, may create a negative pressure differential during use. In accordance with the principles herein, when the MFLP-valve 18 reaches the unsealed condition, or active state, relative to the aperture 25, pressure differential can be normalized by allowing fluid to flow through the aperture 25. In an embodiment, the fluid can be air and the pressure outside of the system can be atmospheric pressure. The direction of the fluid moving through the aperture 25 will depend on whether the pressure differential is positive or negative. The MFLP-valve 18, or a portion thereof, is responsive to a mechanical force applied to open the MFLP-valve 18 upon movable pressure system member 14 of the pressure source 10 of the device approaching or arriving at a selected position. In an embodiment, the selected position can be an initialization position.

In the absence of a MFLP-valve or vent to relieve pressure, it is common for pressure generating devices to have some pressure differential existing between a pressure generating chamber and a volume outside the pressure generating chamber even when it is believed that a volume displacement mechanism of the device has returned to its original position. As such, a desirable feature of the MFLP-valves of the present disclosure is that when the MFLP-valve 18 is in an unsealed condition (i.e., an open position) relative to the aperture 25, any pressure differential existing between a pressure generating chamber and a volume outside the pressure generating chamber in the pressure generating chamber 12 is relieved. Embodiments wherein the pressure generating chamber 12 generates a negative or positive pressure differential between a pressure generating chamber and a volume outside the pressure generating chamber are considered within the scope of the present disclosure. By equalizing the pressure within the pressure generating chamber 12 with pressure outside the pressure generating chamber 12, the pressure generating chamber 12 is returned to a selected pressure, such as atmospheric pressure, if desired. Operating a breastpump or other pressure system in a manner that regularly returns the pressure generating chamber 12 to a selected pressure enhances the accuracy of the pressure system by providing a consistent pressure condition for each cycle of the system.

As illustrated in exemplary embodiments of FIGS. 2-6, an exemplary arrangement of structural components of a pressure source 10 as a movable pressure system member 14 thereof approaches an end wall 20 of a pressure generating chamber 12 is set forth. The pressure source 10 of FIGS. 2-6 is a piston-cylinder-type vacuum source. However, the same principles illustrated in FIGS. 2-6 and described herein could be applied to a diaphragm-type vacuum source, or any other suitable cyclic pressure system in a similar manner.

As illustrated in FIG. 2, the movable pressure system member 14, which is shown in the form of a piston, but could alternatively be a diaphragm or other movable pressure system member, is actuated, such as by an actuator 16 (represented schematically in FIG. 1, but not shown in FIGS. 2-6), which may be a motor or driven by a motor or other applicable mechanical displacement device. The movable pressure system member 14 moves in a direction toward the end wall 20 of the vacuum generating chamber 12, as represented by the vertical up-arrow in FIG. 2.

Figure 5:
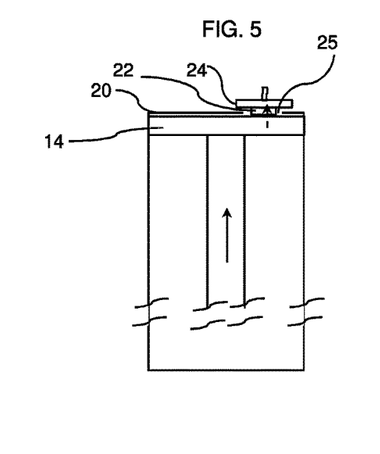
FIG. 5 illustrates the chamber of the pressure source of FIGS. 2-4 as the movable pressure system member approaches the end wall of the chamber.

As illustrated in FIG. 3, the movable pressure system member 14 can initiate contact with a post 22 associated with the MFLP-valve 18 during the course of a pressure cycle. The post 22 may be in the form of a protrusion, such as an exemplary cylindrical protrusion, that extends from a MFLP-valve membrane 24 that normally covers over an aperture 25 provided in any suitable location, such as in the end wall 20 of the vacuum generating chamber 12, which aperture 25 can be seen in FIG. 4. In an alternative embodiment, the post 22 may be located on or connected to the movable pressure system member 14. The continued movement of the movable pressure system member 14 in the direction toward the end wall 20 following initial contact with the post 22 can cause the MFLP-valve membrane 24 of the MFLP-valve 18 to move away from the end wall 20 of the pressure generating chamber 12, as illustrated in FIGS. 4 and 5.

To seal the aperture 25, the MFLP-valve membrane 24 may include a rib, such as an annular rib, that defines a gasket 24a, which may be in the form of an O-ring, as illustrated in FIGS. 4A and 4B. Returning to FIGS. 3 and 4, for the MFLP-valve 18 to seal the aperture 25, the membrane 24 sealingly engages a wall of the pressure generating chamber 12 about a perimeter of the aperture 25. In sealingly engaging a wall of the pressure generating chamber 12 about a perimeter of the aperture 25, the wall may be an end wall of the pressure generating chamber 12 in which the aperture 25 is disposed. The wall of the pressure generating chamber 12 may have surface treatments or features surrounding or near the aperture 25 that complement the composition, size and shape of the membrane 24 (which may include the gasket 24a), enabling a tighter seal at the wall of the pressure generating chamber 12. The surface of the wall of the pressure generating chamber 12 that surrounds the aperture 25 may be sloped inward toward or outward away from the aperture 25, such that the aperture 25 can be sealed with a flat gasket 24a that engages the sloped surface. Alternately, the surface of the wall of the pressure generating chamber 12 that surrounds the aperture 25 may be sloped and the gasket 24a may have a curved shape that is complementary to the sloped surface.

Figure 6:
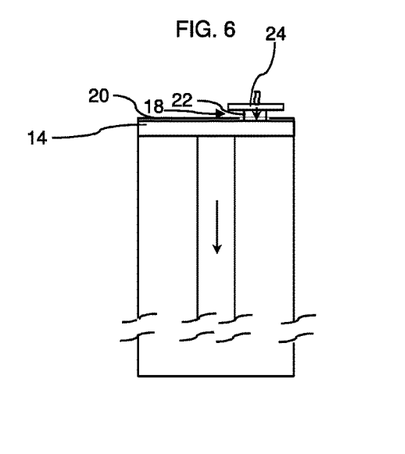
FIG. 6 illustrates the chamber of the pressure source of FIGS. 2-5 once the movable pressure system member reaches an end of its travel within the chamber, and begins to move in a direction away from the end wall, which movement begins to close the MFLP-valve.

As illustrated in the exemplary embodiment of FIG. 6, the movable pressure system member may reverse direction upon reaching a selected position within the pressure generating chamber. The selected position may be near or at the end wall of the pressure generating chamber. The movable pressure system member may also change direction for example, upon the system responding to a parameter other than the MFLP-valve's flag state. This parameter could be a selected minimum volume, an electrical/mechanical condition regarding the actuation or the state of a secondary sensor. As the movable pressure system member reverses, it may also cause the MFLP-valve to begin to move back toward the aperture 25 in the end wall 20 of the vacuum chamber 12. A force such as gravity or another force imposed on the MFLP-valve by the system's geometry may facilitate movement of the MFLP-valve 18 back toward a closed, sealed condition as the movable pressure system member 14 continues to move in a direction away from the end wall 20, i.e., as the movable pressure system member 14 moves away from a position consistent with a minimum volume within the pressure chamber 12. When the movable pressure system member 14 moves sufficiently away from the end wall 20 of the pressure chamber 12 as to lose contact with the post 22 of the MFLP-valve 18, the MFLP-valve membrane 24 of the MFLP-valve 18 returns to its position closing over the aperture 25, i.e., the position of the MFLP-valve 18 illustrated in FIG. 2.

Continued movement of the movable pressure system member 14 away from the end wall 20 generates pressure within the pressure chamber 12 while the MFLP-valve is closed. This pressure may be negative pressure, commonly referred to as vacuum. The vacuum pressure may help to ensure a seal between the MFLP-valve membrane 24 and the end wall 20.

Figure 7:
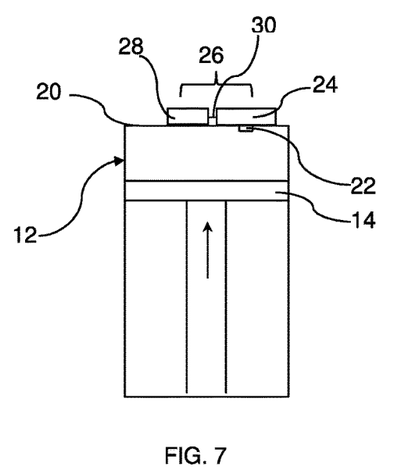
FIG. 7 illustrates an exemplary embodiment of a MFLP-valve including a block secured to an end wall of a pressure chamber secured by a living hinge to a MFLP-valve membrane and post portion of the MFLP-valve.
Figure 8:
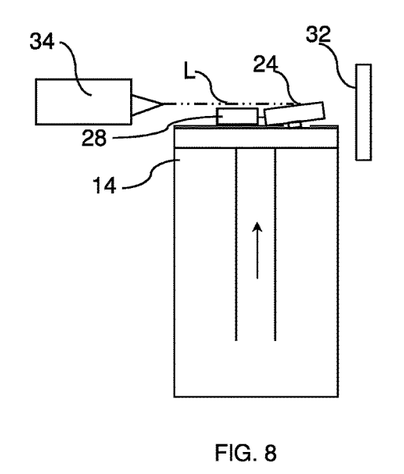
FIG. 8 illustrates the MFLP-valve of FIG. 7 in an unsealed condition, as detected by the interruption of a beam of light directed toward a photosensor.

Turning to FIGS. 7 and 8, an exemplary alternative MFLP-valve 26 is set forth. The alternative MFLP-valve 26 includes an anchoring feature 28 secured to the end wall 20 of the pressure chamber 12. The MFLP-valve membrane 24 of the MFLP-valve 26 may be secured to the anchoring feature 28 by a living hinge 30. When the movable pressure system member 14 contacts the post 22 of the MFLP-valve 26 and continues to move in a direction toward the end wall 20 of the MFLP-valve chamber 12, the MFLP-valve membrane 24 is moved to an unsealed condition. Due to its securement to the anchoring feature 28, the MFLP-valve membrane 24 may be moved to a position at an angle greater than 0° relative to the end wall 20 when in the unsealed condition. This angled position of the MFLP-valve membrane 24 may be advantageous because it provides an opportunity to detect a condition of the MFLP-valve's 26 flag consistent with the movable pressure system member 14 having reached a selected position. The selected position may be a home position. As used herein, a "home position" refers to a position of the movable pressure system member 14 that is closest to the end wall 20 of the pressure chamber 12, or a position consistent with the pressure chamber 12 having a minimal volume in the range of travel of the movable pressure system member 14. If desired, the position sensing function at the MFLP-valve may be selectively decoupled from the pressure modification of the MFLP-valve.

Figure 9:
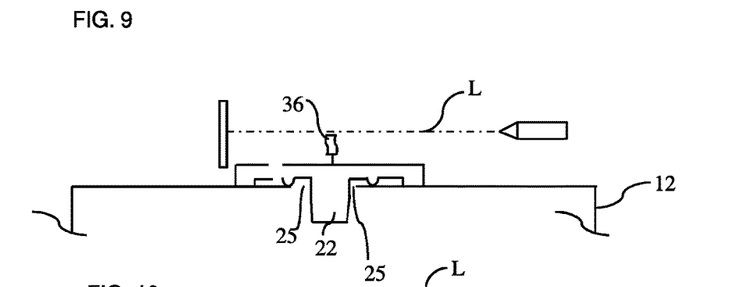
FIG. 9 illustrates an alternate embodiment of a MFLP-valve including a MFLP-valve membrane, an integral sealing gasket, a post that extends through an aperture of a wall of a pressure source, and a trigger in the form of a home flag directly connected to the MFLP-valve membrane that, upon actuation of the MFLP-valve membrane from a sealed to an unsealed condition, interrupts the beam of light directed toward the photosensor.
Figure 10:
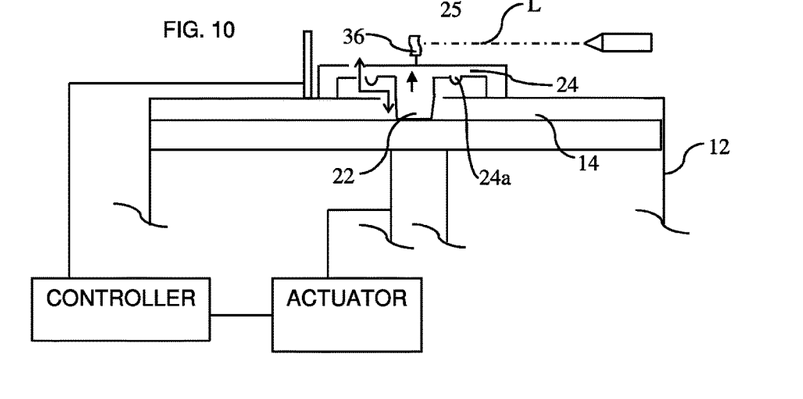
FIG. 10 illustrates the MFLP-valve of FIG. 9 in an unsealed condition, as detected by the interruption of a beam of light directed toward the photosensor.

The home position of the movable pressure system member 14 may be detected, for example, by a photo sensor 32 that detects interruption of a beam of light L projected by a light source 34 toward the photo senor 32, as illustrated in the exemplary embodiment of FIG. 8. The beam of light L may be interrupted by the main body of the MFLP-valve membrane 24. Alternatively, the beam of light L may be interrupted by a home flag 36. The home flag 36 may be directly or indirectly connected to the MFLP-valve membrane 24. As illustrated in FIGS. 1, 9 and 10, such a home flag 36 may be configured to trigger a signal to the controller of the pressure system to at least one of (1) initiate or otherwise modify operation of the pressure source upon motion of the MFLP-valve membrane 24 between a sealed condition and an unsealed condition; and (2) verify a position of the movable pressure system member 14 of the pressure chamber 12.

Various alternate means for detecting at least one of an unsealed condition of the MFLP-valve membrane 24, and a home position of the movable pressure system member 14, may be employed. For instance, instead of interrupting a light beam, the home flag 36 could have an aperture or interruption therein, through which a light beam only passes when the home flag 36 is in a position consistent with the MFLP-valve membrane 24 being in an unsealed condition and/or the movable pressure system member 14 being in the home position. Instead of a light beam, the home flag 36 may be made of a material, such as a conductive metallic material, that completes a circuit, or breaks a circuit, when in a position consistent with the MFLP-valve membrane 24 being in an unsealed condition and/or the movable pressure system member 14 being in the home position. The presence of the home flag 36 in a position consistent with the MFLP-valve membrane 24 being in an unsealed condition and/or the movable pressure system member 14 being in the home position may be detected by a number of alternative sensing mechanisms, for example a magnetic sensor, a proximity switch, or a microswitch.

Alternately, the home flag 36 may comprise a fluid, such as in a gas phase or a liquid phase, wherein the fluid is displaced from a first position to a second position upon movement of the MFLP-valve membrane 24 between a sealed and an unsealed condition and/or the movable pressure system member 14 being in the home position. The movement of the fluid could be detected, which could serve as a signal to the controller of the pressure system to at least one of (1) initiate or otherwise modify operation of the pressure source upon motion of the MFLP-valve membrane 24 between a sealed condition and an unsealed condition; and (2) verify a position of the movable pressure system member 14 of the pressure chamber 12.

Instead of detecting displacement of the MFLP-valve membrane 24 itself or of a home flag 36 directly or indirectly connected to the MFLP-valve membrane 24, the position of the movable pressure system member 14 may be detected, such as through a window in a wall of the pressure generating chamber 12 in conjunction with the action of the MFLP-valve. When the movable pressure system member 14 is detected, a signal may be sent to a controller. In combination with the action of the MFLP-valve, detection of the movable pressure system member 14 may also be used to initiate or change the motion of the movable pressure system member 14, allowing continued operation of the pressure system. The detection of the movable pressure system member 14 and the opening of the MFLP-valve membrane 24 may be coordinated to occur in a complementary way, but they need not occur simultaneously.

The drawing figures illustrate an aperture 25 located at the end of the pressure generating chamber 12 that coincides with an end of range of motion of the movable pressure system member 14. This end of range of motion may be consistent with a minimum volume within the pressure generating chamber 12. While this "home position" of the movable pressure system member 14 may be considered the beginning of a stroke or cycle, the aperture 25 may alternately be positioned to trigger anywhere along the pressure cycle. For example, the aperture 25 may be located at a position of the pressure generating chamber 12 that coincides with an opposite end of range of motion of the movable pressure system member 14, consistent with a maximum volume within the pressure generating chamber 12. Depending on the construction and operation of the given pressure generating chamber 12 and movable pressure system member 14, this position may be the middle of a pressure cycle or the end of a stroke of the movable pressure system member 14. The MFLP-valve 18 may be placed at any location in the system that provides a beneficial position indication, or relief of pressure differential.

Figure 11:
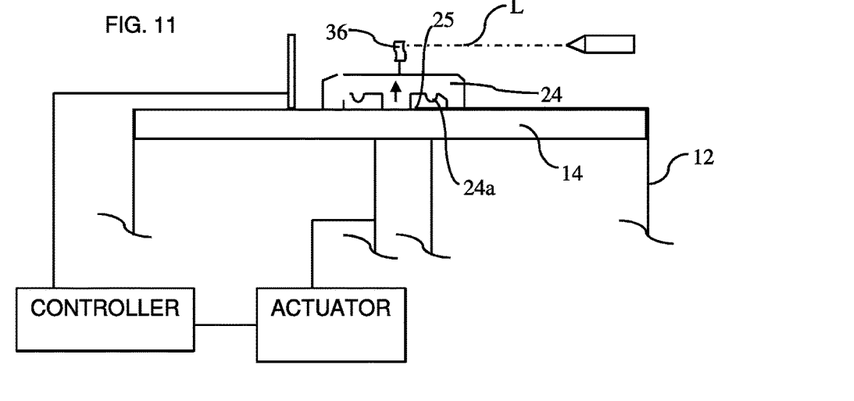
FIG. 11 illustrates a configuration similar to that of FIG. 10, once the movable pressure system member reaches an end of its travel within the chamber.

The MFLP-valve 18 may have a region 24b (see FIGS. 10 and 11), such as a perimeter region, that, like the anchor 28 of the embodiment illustrated in FIGS. 7 and 8, serves to fix the MFLP-valve 18 to a wall of the pressure generating chamber 12. A MFLP-valve membrane portion 24 of the MFLP-valve 18 remains sufficiently flexible to selectively move the gasket 24a out of sealing engagement with the perimeter of the aperture 25 when the post 22 of the MFLP-valve 18 is engaged by the movable pressure system member 14. The MFLP-valve 18 may be attached to the pressure system in number of ways, including but not limited to fasteners, retaining clips, barbs, clamps or adhesives. It is important that the attachment method positions the sealing element in such a way that it can engage the aperture in the pressure system at the appropriate time, as previously discussed. The attachment method, in conjunction with the composition and geometry of the MFLP-valve, may be designed to allow the MFLP-valve to open in response to a selected pressure, irrespective of the position of mechanical elements in the system.

Figure 12:
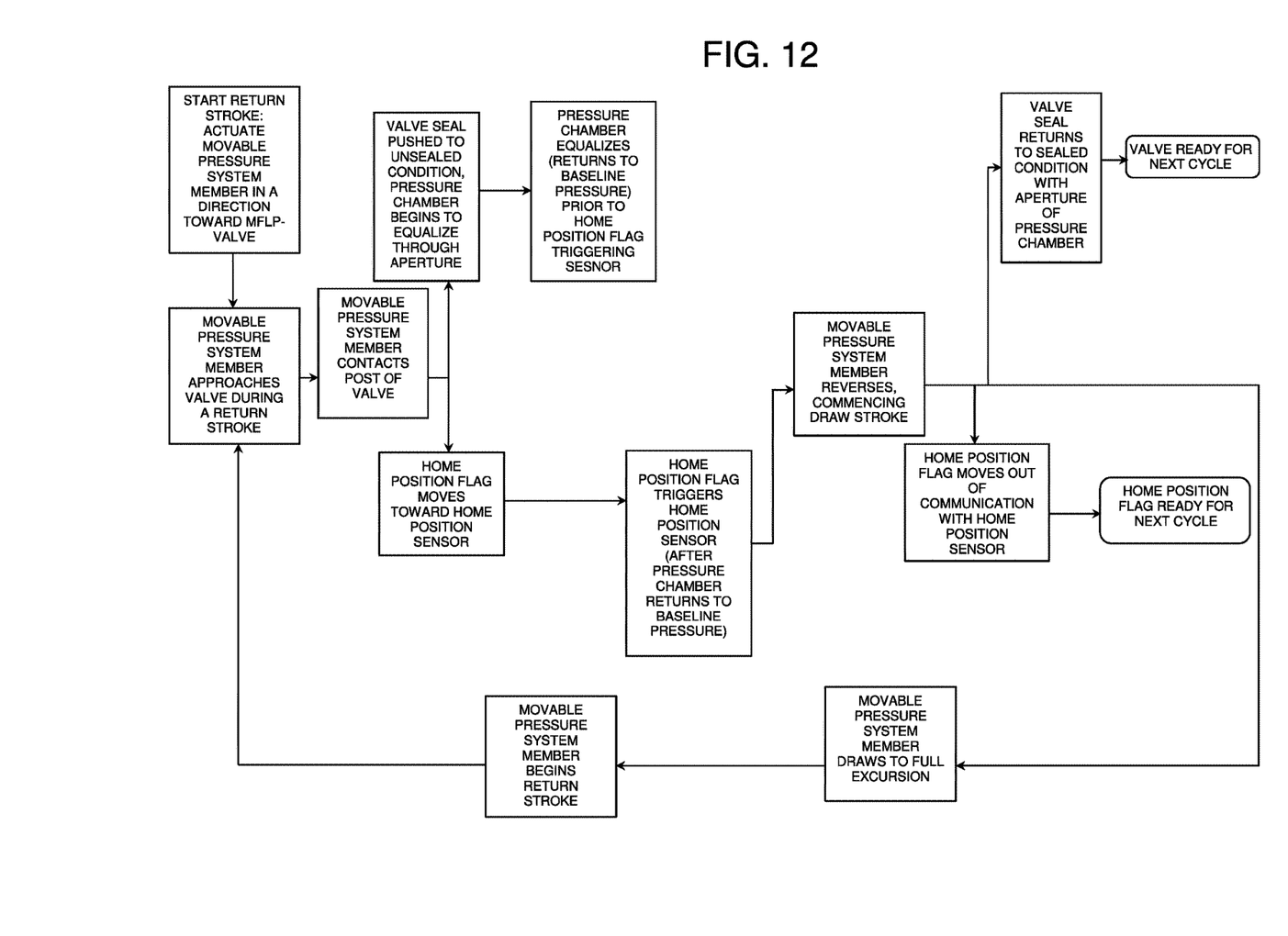
FIG. 12 is a flowchart depicting operation of a pressure system featuring a vacuum equalization MFLP-valve of the present disclosure.

As illustrated in the exemplary embodiment of FIG. 12, the movable pressure system member 14 approaches the MFLP-valve 18 during a return stroke. Next, the movable pressure system member 14 contacts the post 22 of the MFLP-valve 18. Then, the home flag 36, referred to in the flow diagram as a "home position flag", moves toward a home position sensor as a MFLP-valve seal is pushed to an unsealed condition. The unsealing of the aperture 25 results in the pressure chamber 12 beginning to equalize through the aperture 25.

In an embodiment wherein the pressure system is a breastpump, the movable pressure system member can be a piston or diaphragm, and the pressure chamber can be a cylinder, the pressure chamber 12 equalizes (returns to a selected pressure), prior to the home flag 36 triggering the home position sensor (though it is recognized that the home flag 36 could trigger the home position sensor at any time subsequent to contact between the movable pressure system member 14 and the post 22 of the MFLP-valve 18). Next, the home flag 36 triggers the home position sensor. Thereafter, the movable pressure system member 14 reverses, and commences its draw stroke. This can cause the home position flag 36 to move out of communication with the home position sensor. After the movable pressure system member 14 disengages from the post 22 of the MFLP-valve 18, the MFLP-valve 18 returns to a sealed condition with the aperture 25 of the pressure chamber 12. This seal may be enhanced by the negative pressure increase as the movable pressure system member 14 continues its draw stroke. The MFLP-valve 18 and its associated home position flag 36, are then ready for the next cycle. Ultimately, the movable pressure system member 14 draws to its intended excursion, then begins a return stroke and the cycle repeats.

Figure 13:
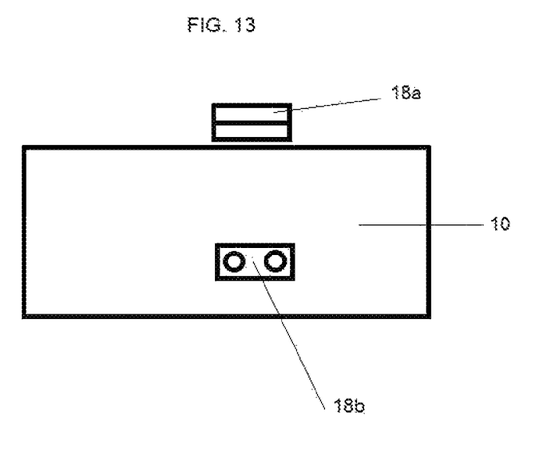
FIG. 13 is a schematic illustration of an exemplary pressure system, including two MFLP-valves constructed in accordance with the principles described herein.

Referring to FIG. 13, a schematic illustration of a pressure source 10 is disclosed. The pressure source 10 can include multiple MFLP-valves 18a and 18b constructed in accordance with the principles disclosed herein. A single MFLP-valve 18 could be used instead of two MFLP-valves 18, or additional MFLP-valves 18 could be provided, if desired.

The pressure source 10 may be configured to selectively activate one or more MFLP-valves based on the systems mode of operation. Each MFLP-valve may be independently configured in terms of geometry, material, tuning condition, or the presence of a position indicating flag. For example, in FIG. 13, MFLP-valve 18a has a vented region that can expand and contract based on the mechanical action of pressure source 10, while MFLP-valve 18b has one or more nonexpandable vents that are connected to and disconnected from the pressure source 10 based on mechanical action. Having multiple MFLP-valves with differing configurations, each of which can be independently activated or deactivated, may be beneficial in a system that includes multiple modes of operation.

Figure 14:
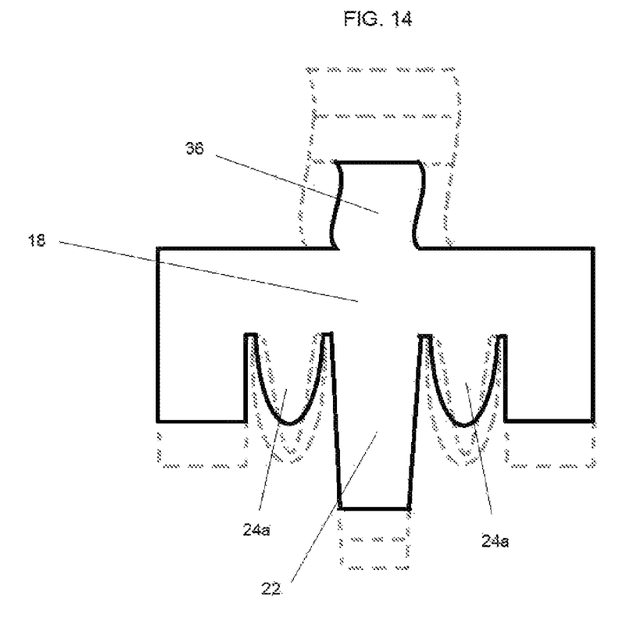
FIG. 14 is a side view of an exemplary MFLP-valve constructed in accordance with the principles herein, where one or more component of the MFLP-valve may be fine-tuned in any manner, such as illustrated by the broken lines, to meet the needs of a particular pressure system with which the MFLP-valve is employed.

Turning to FIG. 14, while an exemplary MFLP-valve 24 is illustrated in solid lines, various features of the MFLP-valve 24 can be adjusted to tune the accuracy, precision, sensitivity, or other parameter associated with the MFLP-valve 24. This adjustment may occur as a factory setting, or it may occur after initial manufacturing, as part of the function of the overall system. If a pressure system, such as a breastpump, is configured to offer selectable or alternative modes of operation for a user, it may be beneficial to incorporate a MFLP-valve, constructed in accordance with the principles herein, having performance characteristics which can be selectively tuned as a result of user action. This tuning may be accomplished by configuring the system to reposition, compress, expand, trim, energize, or otherwise modify a portion of the MFLP-valve, or an interface associated with the MFLP-valve, as a result of user action. Various examples of tunable features of the MFLP-valve 24 are represented by dashed lines in FIG. 14. These include, but are not limited to, the home flag 36 that interacts with the position switch or position sensor, the element(s) that attach the MFLP-valve to the rest of the system, the gasket 24a that surrounds and/or is inserted into the relief orifice, and the post 22 that contacts the movable pressure system member 14. For instance, the home flag 36 may be varied in height, width, or any other dimension in order to adjust its ability to be detected. Another example, the gasket 24a may be an O-ring or may have a different shape and the diameter and/or size of the gasket 24a may be varied to best achieve sealing around an aperture 25. The mating properties between the gasket 24a and the wall surrounding the aperture 25 may be varied. As yet another example, the height of the post 22 may be altered to vary when the post 22 is impacted by the movable pressure system member 14. In addition to the geometric properties of the various elements of the MFLP-valve 24, the material properties of any of the elements of the MFLP-valve 24 may be altered in order to tune parameters associated with the MFLP-valve 24. For example, the compressibility, stiffness, or elasticity of the post 22 may be altered to change the interaction between the post 22 and the movable pressure system member 14 and/or the timing of the pressure cycles. Elastic, rubber, spring-like material, or any other expandable material could be used in the MFLP-valve 24. The MFLP-valve may be a single component or it may be composed of more than one component or material. In addition, the performance of the MFLP-valve 18 may be tuned by altering the elements of pressure source 10 with which the MFLP-valve 18 interacts.

Figure 15:
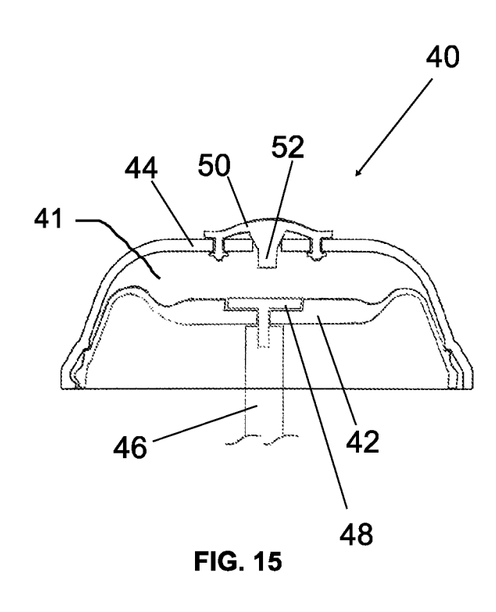
FIG. 15 is a cross-sectional view of an alternate embodiment wherein an MFLP-valve of the present disclosure is employed in a rigid cap portion of a diaphragm-type pressure source, with a flexible diaphragm portion of the pressure source, under the control of a movable pressure system member, illustrated in a first position away from a rigid cap.

Implementation of an MFLP-valve of the present disclosure in diaphragm-type pressure sources will now be described. As illustrated in FIG. 15, a diaphragm-type pressure source 40 may include a flexible diaphragm membrane 42 and a rigid cap 44. A movable pressure system member 46, such as a piston, actuates the flexible diaphragm membrane 42 between a first position away from the rigid cap 44 and a second position toward the rigid cap 44. The movable pressure system member 46 may be provided with a rigid engagement member 48 that passes through the surface of the flexible diaphragm membrane 42. An MFLP-valve 50 is connectable in any suitable manner, such as by providing connecting members 45 that extend through the cap 44. Alternatively, the connecting members can be securely fitted within the volume of the rigid cap 44.

Figure 16:
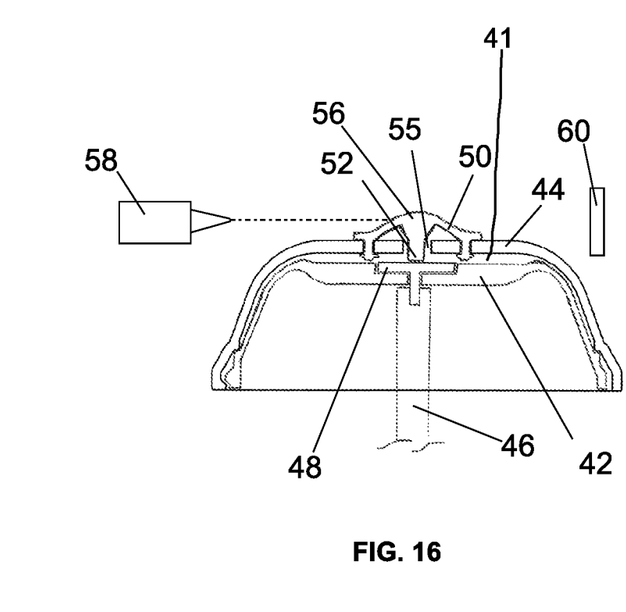
FIG. 16 is a cross-sectional view of the embodiment of FIG. 16, with the flexible diaphragm portion of the pressure source, under the control of the movable pressure system member, illustrated in a second, home position toward the rigid cap, with the movable pressure system member contacting an exemplary post of the MFLP-valve associated with the pressure source, causing the MFLP-valve to begin to move in the same direction as the movable pressure system member, resulting in the MFLP-valve exposing a region of an interior of the chamber between the flexible diaphragm portion and the rigid cap of the pressure source to an initializing pressure through an exemplary aperture in the rigid cap that is otherwise closed by the post of the MFLP-valve.

As illustrated in FIG. 16, when the movable pressure system member 46 actuates the flexible diaphragm membrane 42 to the second position toward the rigid cap 44, the rigid engagement member 48 contacts a post 52 of the MFLP-valve 50. Due to the engagement of the rigid engagement member 48 with the post 52 of the MFLP-valve 50, further movement of the movable pressure system member 46 toward the rigid 44 causes the post 52 of the MFLP-valve 50 to move out of sealed engagement with a vent aperture 55 in the rigid cap 44. The unsealing of the vent aperture 55 results in the pressure chamber 41, and specifically the region between an inner wall of the rigid cap 44 and the flexible diaphragm membrane 42, equalizing through the aperture 55. The MFLP-valve 50 may be provided with a flag or other sensor-trigger to facilitate detection that the flexible diaphragm membrane 42 or the movable pressure system member 46 has reached the home position. Alternately, a portion of the surface of the MFLP-valve 50 itself, such as an apex 56 of an operable cover of the MFLP-valve 50, may serve as the flag or other sensor trigger. By way of example only, actuation of the post 52 of the MFLP-valve 50 and movement out of sealed engagement with the vent aperture 55 in the rigid cap 44, the apex 56 may interrupt a beam of light from a light source 58 normally detected by a photosensor 60. Alternately, a Hall effect position sensor or other position sensor could be used in concert with the apex or other surface of the MFLP-valve 50, or with a flag associated with the MFLP-valve 50 to detect that the flexible diaphragm membrane 42 or the movable pressure system member 46 has reached the home position.

Figure 17:
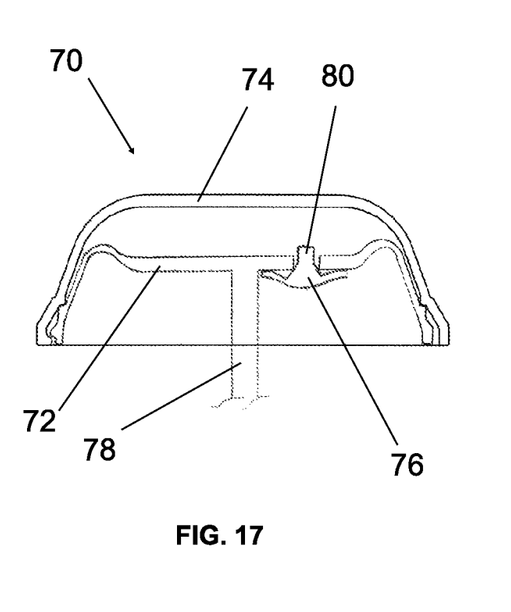
FIG. 17 is a cross-sectional view of another alternate embodiment wherein an MFLP-valve of the present disclosure is employed in a flexible diaphragm portion of a diaphragm-type pressure source, with the flexible diaphragm portion of the pressure source, under the control of a movable pressure system member, illustrated in a first position away from a rigid cap.
Figure 18:
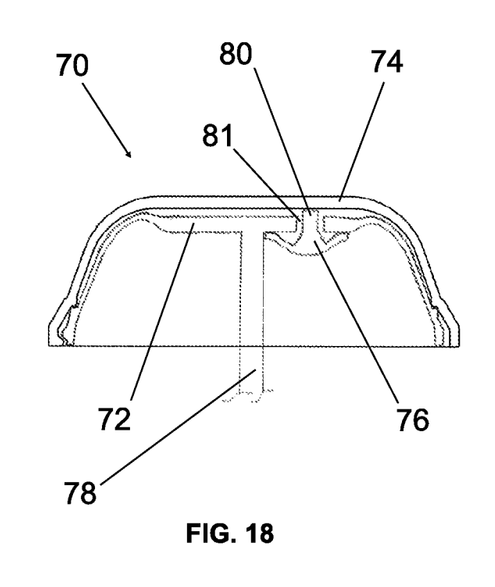
FIG. 18 is a cross-sectional view of the embodiment of FIG. 17, with the flexible diaphragm portion of the pressure source, under the control of the movable pressure system member, illustrated in a second, home position toward the rigid cap, with the movable pressure system member bringing an exemplary post of the MFLP-valve associated with the diaphragm portion of the pressure source into engagement with the rigid cap, causing the MFLP-valve to begin to move in a direction opposite to the movable pressure system member, causing the MFLP-valve to expose a region of an interior of the chamber between the flexible diaphragm portion and the rigid cap of the pressure source to an initializing pressure through an exemplary aperture in the rigid cap that is otherwise closed by the post of the MFLP-valve.

An alternate embodiment of the use of an MFLP-valve of the present disclosure in a diaphragm-type pressure source is illustrated in FIGS. 17 and 18. In this embodiment, a diaphragm-type pressure source 70 includes a flexible diaphragm membrane 72 and a rigid cap 74. Instead of the MFLP-valve being provided in the rigid cap 74, in this embodiment an MFLP-valve 76 is provided in the flexible diaphragm membrane 72. The flexible diaphragm membrane 72 is actuated by a movable pressure system member 78, such as a piston, from a first position away from the rigid cap 74, as illustrated in FIG. 17, to a second, home position toward the rigid cap, as illustrated in FIG. 18.

The MFLP-valve 76 is provided with a post 80 that extends from an operable cover of the MFLP-valve 76, through a vent aperture 81 in the flexible diaphragm membrane 72. The post 80 seals the vent aperture 81 when the post 80 is not engaging the rigid cap 74. During actuation by the movable pressure system member 78 of the flexible diaphragm membrane 72 toward the home position, as illustrated in FIG. 18, the post 80 of the MFLP-valve 76 makes contact with the rigid cap 74, and continued actuation of the movable pressure system member 78 causes the post 80 to unseal the vent aperture 81, thereby equalizing pressure in the space between the flexible diaphragm membrane 72 and the rigid cap 74.

Because the MFLP-valve 76 of this embodiment opens underneath the flexible diaphragm membrane 72, it may be more involved to arrange a sensor that can be used to detect the arrival of the flexible diaphragm membrane 72 or the movable pressure system member 78 at the home position. However, a sensor, such as a photoelectric sensor or a Hall effect position sensor, could be arranged within the diaphragm membrane 72. Alternately, a contact pad may be provided on the underside of the rigid cap 74 in registration or alignment with the post 80 of the MFLP-valve 76, and each time the post 80 contacts the contact pad, a signal could be communicated to a controller indicative of arrival of the flexible diaphragm membrane 72 or the movable pressure system member 78 at the home position.

While the components and features disclosed herein are illustrated and described with respect to certain specific embodiments, it will be understood that combinations and sub-combinations of those components and features can be accomplished within the scope of this specification, and such combinations and sub-combinations should also be considered as disclosed herein.

The embodiments herein have been described and shown for purposes of illustration only, and are not to be construed as constituting any limitations of the present principles. Modifications will be obvious to those skilled in the art, and all modifications that do not depart from the spirit of the principles herein are intended to be included within the scope of the appended claims. Those skilled in the art will appreciate that the conception, upon which this disclosure is based, may readily be utilized as a basis for the designing of other structures, methods and systems for carrying out the several purposes of the present principles.

Therefore, the foregoing is considered as illustrative only of the principles herein. Further, since numerous modifications and changes will readily occur to those skilled in the art, it is not desired to limit the principles to the exact construction and operation shown and described, and accordingly, all suitable modifications and equivalents may be resorted to, falling within the scope of the principles described herein.

What is claimed is:

1. A breastmilk expression system comprising:
   a movable pressure system member disposed in the system, the movable pressure system member configured for movement between a first position and a second position, further comprising:
   a MFLP-valve configured to minimize a pressure differential between a pressure generating chamber and a volume outside the pressure generating chamber through an aperture, the MFLP-valve actuable to an open position upon the movable pressure system member reaching the second position and the MFLP-valve indicating a position to a sensor in the system;
   wherein the movable pressure system member is a piston configured to generate a vacuum within the pressure generating chamber; and
   wherein the valve includes a post extending through the aperture, the post being selectively engaged by the piston, actuation of the valve from a first, sealed position sealing the aperture and a second, open position unsealing the aperture initiated by the piston coming into contact with the post.

2. The breastmilk expression system of claim 1, wherein the MFLP-valve is configured to be responsive to a mechanical force applied thereto and is configured to open as the movable pressure system member arrives at the second position and operably connects to the valve, thereby providing the mechanical force applied to the MFLP-valve.

3. The breastmilk expression system of claim 1 configured to verify a position of the movable pressure system member.

4. The breastmilk expression system of claim 1 removably connected and adaptable within a volume of a rigid cap.

5. The breastmilk expression system of claim 1, wherein the MFLP-valve extends through a flexible diaphragm membrane.

6. The breastmilk expression system of claim 1, the MFLP-valve further including a membrane surrounding the post, the membrane having a surface area greater than an area of the aperture in the pressure generating chamber through which the post extends, such that upon disengagement of the post by the reciprocating member, the membrane closes over the aperture.

7. The breastmilk expression system of claim 6, the MFLP-valve further including a gasket depending from the membrane such that upon disengagement of the post by the reciprocating member, the gasket sealingly engages the pressure generating chamber about a perimeter of the aperture.

8. The breastmilk expression system of claim 5, the MFLP-valve including a living hinge, the living hinge hingedly securing the membrane to a portion of the MFLP-valve, the MFLP-valve being secured to the wall of the pressure generating chamber.

9. The breastmilk expression system of claim 1; and
   a controller in operable communication with a pressure source of the system; and a flag connected to the MFLP-valve, the flag configured to trigger at least one of
   (1) modify operation of the pressure source upon motion of the MFLP-valve between a sealed condition and an unsealed condition, and
   (2) verify a position of the movable pressure system member of the system.

10. The breastmilk expression system of claim 9, wherein the flag is directly attached to the MFLP-valve.

11. The breastmilk expression system of claim 9, wherein the flag is indirectly attached to the MFLP-valve.

* * * * *